US00PP11307P

United States Patent [19]

Zaiger et al.

[11] Patent Number: Plant 11,307

[45] Date of Patent: Mar. 21, 2000

[54] APRICOT TREE NAMED 'BONNY'

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, Calif. 95358

[21] Appl. No.: 09/066,833

[22] Filed: Apr. 27, 1998

[51] Int. Cl.[7] ..... A01H 5/00

[52] U.S. Cl. ..... Plt./186

[58] Field of Search ..... Plt./186

[56] References Cited

U.S. PATENT DOCUMENTS

P.P. 4,673 3/1981 Peters ..... Plt./186
P.P. 8,433 10/1993 Zaiger et al. ..... Plt./186

*Primary Examiner*—Howard J. Locker
*Assistant Examiner*—Wendy A Baker

[57] ABSTRACT

Our new and distinct variety of apricot tree (*Prunus armeniaca*) has the following unique combination of outstanding features that are desirable in a new variety. The following descriptive features of the tree and its fruit were characterized with the tree budded on Nemaguard (non-patented) rootstock, grown on Hanford sandy loam soil, Storie Index rating 95, in U.S.D.A. Hardiness Zone 9, near Modesto, Calif., and with standard commercial cultural fruit growing practices, such as, pruning, thinning, spraying, irrigation and fertilization:

1. Heavy and regular production of fruit.

2. Fruit with good flavor and eating quality, both fresh and canned.

3. Fruit with firm flesh, good handling and shipping quality.

4. Vigorous, semi-spreading growth.

5. Fruit that maintains good texture, shape and appearance after being canned.

6. Fruit with a high degree of soluble solids (average 14.1° Brix).

1 Drawing Sheet

ORIGIN OF THE VARIETY

The new and distinct variety of apricot tree was originated by us in our experimental orchard located near Modesto, Calif., from seed collected from an open pollinated apricot seedling of unknown parentage. A large number of seedlings were grown on their own root system and maintained under close observation, one seedling, which is the present variety, evidenced the outstanding fruit characteristics described above and was selected for asexual propagation and commercialization.

ASEXUAL REPRODUCTION OF THE VARIETY

Asexual reproduction of the new and distinct variety of apricot tree was by budding to Nemaguard (non-patented) rootstock, as performed by us in our experimental orchard located near Modesto, Calif., and shows that all characteristics of the tree and its fruit run true to the original tree and are established and transmitted through succeeding asexual propagations.

SUMMARY OF THE VARIETY

The new and distinct variety of apricot tree is of large size, vigorous, semi-spreading growth; a regular and productive bearer of medium to large, yellow-orange, freestone fruit, with good flavor and eating quality, both fresh and canned. The tree is further characterized by producing fruit that has firm flesh, good handling and shipping quality, being nearly uniform in size throughout the tree and, in comparison to Tri-Gem Apricot (U. S. Plant Pat. #6755), the fruit of the new variety is approximately 5 days later in maturity.

PHOTOGRAPH OF THE VARIETY

The accompanying color photographic illustration shows typical specimens of the foliage and fruit of the present new apricot variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of apricot tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Pruned to approximately 12 to 14 feet in height at maturity for economical harvesting of fruit.

*Vigor.*—Vigorous. Growth in the first growing season is approximately 5 to 7 feet in height and 5 to 6 feet in width. Pruned in the late fall or early winter to select desirable primary scaffolds, reducing height to approximately 4 to 5 feet. Growth rate will vary slightly with type and depth of soil, cultural practices and climatic conditions.

*Form.*—Semi-spreading. Tree pruned to open center of tree for more light penetration and to select scaffolds which will carry a heavy crop load. Heavy production of fruit develops semi-spreading conditions.

*Productivity.*—Productive. Fruit set varies from one to several times more than desirable crop load. Fruit set is reduced and spaced by thinning to produce desirable marketable size. Number of fruit set varies with climatic conditions, primarily at bloom time.

*Bearer.*—Regular. Fruit thinning varied from light to heavy over a 5 year period. Number and size of fruit vary slightly with tree spacing, soil conditions and cultural practices.

*Density.*—Medium dense. Foliage from numerous branches and twigs growing throughout the center of the tree are removed to allow more sunlight and air movement, which enhances fruit color, soluble solids and spurring of fruit wood.

Trunk:

*Size.*—Large. Circumference of 18 inches measured on an 8 year old tree, 10 inches above ground. Circumference may vary with type of soil, fertilization and cultural practices.

*Texture.*—Medium shaggy.

*Color.*—Soot brown to dark brown (5—D—3) to (5—E—6).

Branches:

*Size.*—Medium. Circumference varied from 6 to 9 inches measured 3 feet above ground. Scaffolds and lateral branches selected with proper angles to carry heavy crop load.

*Texture.*—Smooth to medium rough, varies with age of growth.

*Lenticels.*—Large size. Numerous. The average number of lenticels on a 4 inch square surface varied from 45 to 49 approximately 3 feet above ground. The length varied from 3/32 to 7/32 inch and 1/32 to 3/32 inch width. The lenticels decrease in size on smaller branches.

*Color.*—Brown to tobacco brown (5—E—6) to (5—F—6).

Leaves:

*Size.*—Large. Average length 5 inches. Average width 2 7/8 inches.

*Form.*—Ovate, pointed.

*Margin.*—Serrate.

*Thickness.*—Medium.

*Surface.*—Smooth.

*Petiole.*—Average length 1 1/4 inches. Medium width.

*Glands.*—Globose. Number varies from 1 to 3. Average number 2. Small size. Located on upper portion of petiole and lower portion of leaf blade. Color — reddish brown to dark brown (8—F—4) to (8—F—6).

*Color.*—Upper surface — green to dark green (28—F—6) to (28—F—8). Lower surface — dull green to green (28—E—6) to (28—E—8).

Flower buds:

*Size.*—Medium to large.

*Length.*—Medium.

*Form.*—Plump, blunt.

*Pubescence.*—Pubescent.

*Flower:*

*Size.*—Large, showy. Average height 5/8 inch. Average diameter 1 3/16 inches.

*Pollen.*—Present — self fertile.

*Blooming Period.*—Date of First Bloom Feb. 15, 1997. Date of Last Bloom Feb. 21, 1997. Varies slightly with climatic conditions.

*Fragrance.*—Very slight.

*Petal.*—Petal shape nearly orbicular, slightly narrower at point of attachment. Edges vary from straight to slightly scalloped.

*Color.*—Pink to light pink (11—A—4) to (11—A—2). Color fades with age of flowers.

Fruit:

*Maturity When Described.*—Firm ripe.

*Date of First Picking.*—Jun. 8, 1997.

*Date of Last Picking.*—Jun. 13, 1997. Varies slightly with climatic conditions.

*Size.*—Medium to large. Average diameter axially 2 inches. Average transversely in suture plane 2 inches. Average diameter measured at right angles to suture plane 1 7/8 inches.

*Weight.*—Average weight 73 grams, varies from 65 grams to 80 grams. Weight of fruit varies slightly with soil fertilization, amount of thinning and climatic conditions.

*Form.*—Nearly globose, slightly flattened toward suture plane.

*Suture.*—Pronounced, extends from base to apex.

*Ventral Surface.*—Lipped, well sealed.

*Apex.*—Slightly retuse.

*Base.*—Retuse.

*Cavity.*—Rounded. Average depth — 1/4 inch. Average breadth — 3/8 inch.

Flesh:

*Ripens.*—Evenly.

*Texture.*—Firm.

*Fibers.*—Few, small, tender.

*Aroma.*—Abundant.

*Amygdalin.*—Undetected.

*Juice.*—Moderate amount, enhances flavor, good balance between sugar and acid. Average Brix 14.1°, varies from 12.7° to 16°. Brix varies slightly with number of fruit per tree and climatic conditions during fruit maturity.

*Eating Quality.*—Good, both fresh and canned.

*Flavor.*—Good.

*Color.*—Yellow to light orange (6—A—4) to (6—A—6). Pit cavity — light orange to orange (6—A—6) to (6—B—6).

Stem:

*Size.*—Average length 7/32 inch. Average width 1/8 inch.

*Color.*—Olive yellow to olive green (3—D—7) to (3—E—8).

Skin:

*Thickness.*—Medium.

*Texture.*—Medium.

*Down.*—Medium amount, short in length.

*Tendency to Crack.*—Very slight.

*Color.*—Light orange to orange (5—A—5) to (6—A—6).

Stone:

*Type.*—Freestone.

*Size.*—Medium. Average length 1 inch. Average width 7/8 inch. Average thickness 5/8 inch.

*Form.*—Ovoid.

*Base.*—Straight, short in length.

*Apex.*—Rounded.

*Surface.*—Very lightly pitted throughout. Two long narrow ridges, one on each side of suture.

*Sides.*—Varies from equal to unequal.

*Tendency to Split.*—None.

*Color.*—Brown to dark brown (5—E—6) to (5—F—6).

Use: Dessert. Culinary. Market, local and long distance.

Keeping quality: Good. Fruit stored for 21 days at 38° to 42° F. and showed no internal browning or wooliness of flesh.

Shipping quality: Good. Fruit showed minimal scarring or bruising of skin or flesh during packing and shipping trails.

Culinary: Each side of fruit halves held shape, color and attractiveness after being canned. Flavor of canned fruit evaluated good to very good.

The present new variety of apricot tree, its flowers, foliage and fruit herein described may vary in slight detail due to climate, soil conditions and cultural practices under which the variety may be grown. The present description is that of the variety grown under the ecological conditions prevailing near Modesto, Calif.

Claim:

1. A new and distinct variety of apricot tree, substantially as illustrated and described, characterized by its large size, vigorous, semi-spreading growth and being a productive and regular bearer of medium to large, firm, freestone fruit with good flavor and eating quality, both fresh and canned; the fruit is further characterized by maintaining good texture, shape and appearance after being canned; having firm flesh with good handling and shipping quality and, in comparison to the Tri-Gem Apricot (U. S. Plant Pat. #6755), the fruit of the new variety is approximately 5 days later in maturity.

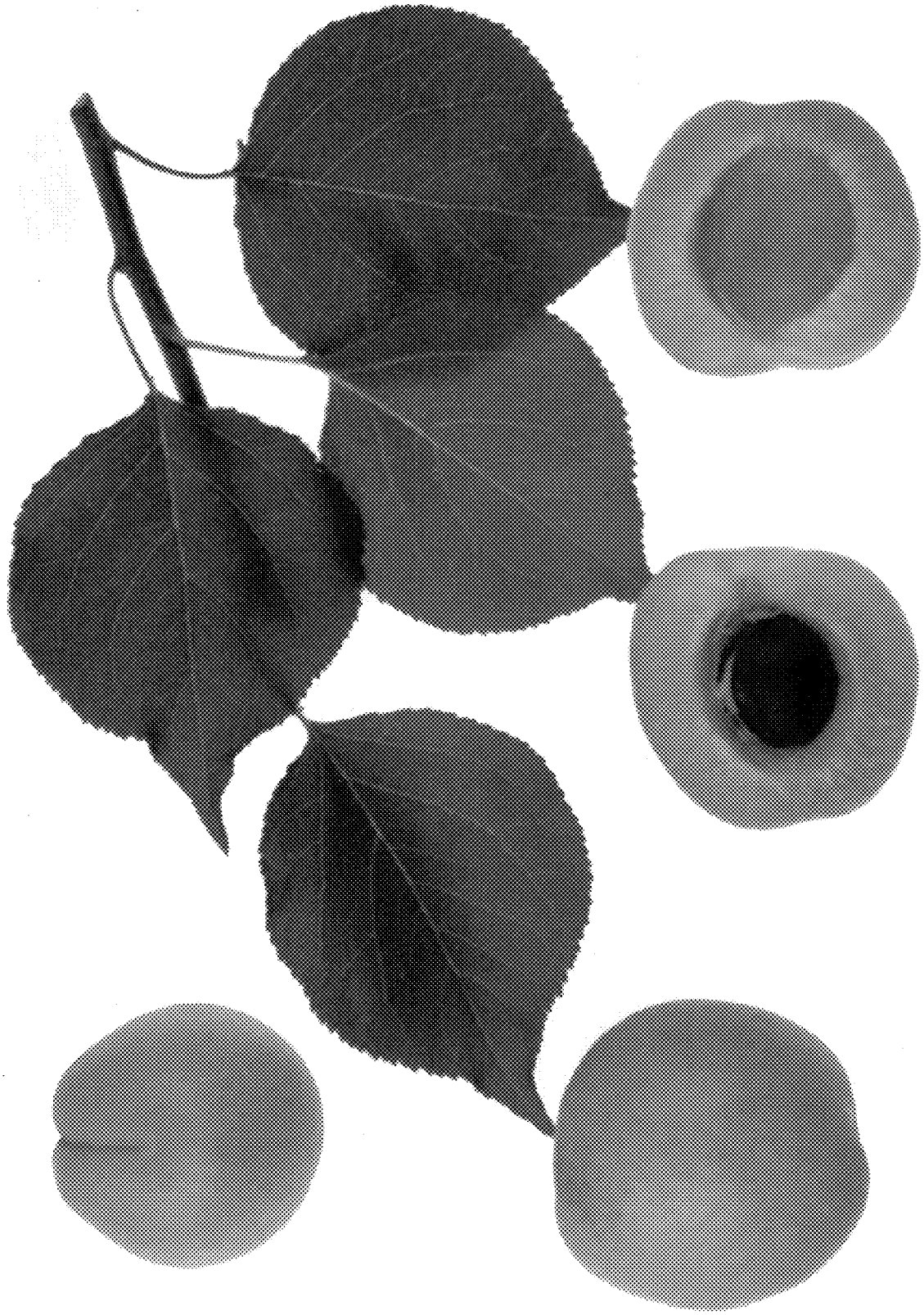

* * * * *